US00PP11704P

United States Patent [19]

Konishi

[11] Patent Number: Plant 11,704

[45] Date of Patent: Dec. 19, 2000

[54] DELPHINIUM PLANT NAME 'PLAGU LIGHT PURPLE'

[75] Inventor: Kunihiro Konishi, Nagano, Japan

[73] Assignee: Japan Tobacco, Inc., Tokyo, Japan

[21] Appl. No.: 09/163,568

[22] Filed: Sep. 30, 1998

[30] Foreign Application Priority Data

Oct. 29, 1997 [JP] Japan ..... 10325

[51] Int. Cl.[7] ..... A01H 5/00

[52] U.S. Cl. ..... Plt./263

[58] Field of Search ..... Plt./263

*Primary Examiner*—Howard J. Locker
*Assistant Examiner*—Michelle Kizilkaya
*Attorney, Agent, or Firm*—Birch, Stewart, Kolasch & Birch, LLP

[57] ABSTRACT

The present invention relates to a new and distinct garden variety of delphinium. This delphinium, denominated 'Plagu Light Purple', is a mutant derived from a delphinium variety 'Plagu Blue'. The present delphinium is characterized by its sepals assuming a vivid purple color with a dash of blue.

2 Drawing Sheets

BACKGROUND OF THE INVENTION

Delphiniums are garden plants belonging to the family Ranunculaceae, and they flower around June to August under natural conditions in the open air.

Delphinium flowers have a variety of colors including blue, white and cream. The major color is blue. Since delphiniums prefer a cool and dry climate, they are cultivated in England and in California, the United States for use as garden flowers or cut flowers. However, the introduction of delphinium cultivation has hardly been successful in the southwestern warm area of Japan where the climate is hot and humid.

Because of their vivid colors, the demand for delphiniums has been greatly increased in recent years. In response to this increase in demand, various new varieties have been bred. However, the new varieties have not necessarily satisfied the demand sufficiently and the breeding of more attractive new varieties is desired.

The present invention has been made to meet such demand. It is the object of the present invention to provide a new and distinct variety of delphinium.

The breeding of the delphinium of the invention was carried out at the present inventor's farm located at 55, 3520, Tokiwa, Ohmachi City, Nagano Pref., Japan and the Applied Plant Research Laboratory of Japan Tobacco Inc. located at Ohaza-Idei 1900, Oyama City, Tochigi Pref., Japan from 1995 through 1997. The delphinium of the present invention occurred as a naturally occurring branch mutation of unknown origin. The present delphinium is a hybrid of *Delphinium belladonne* and *Delphinium elatum.*

In 1995, the inventor found among delphinium plants of 'Plagu Blue' (unpatented) obtained from cultured tissue a mutant whose sepals assumed a purple color with a dash of vivid blue that was different from the color of sepals in 'Plagu Blue' (i.e., a dark blue color with a dash of purple). The axillary buds of this mutant were collected and grown by tissue culture. The resultant young plants were planted in October, 1996. Thereafter, flowering inspection of these plants obtained from cultured tissue was performed in January, 1997 to thereby confirm that their characteristics are stable. Thus, the breeding has been completed.

SUMMARY OF THE INVENTION

The most remarkable characteristic of the delphinium of the invention is that its sepals assume a purple color with a dash of vivid blue.

BOTANICAL DESCRIPTION

Plant Body

Figure 1:
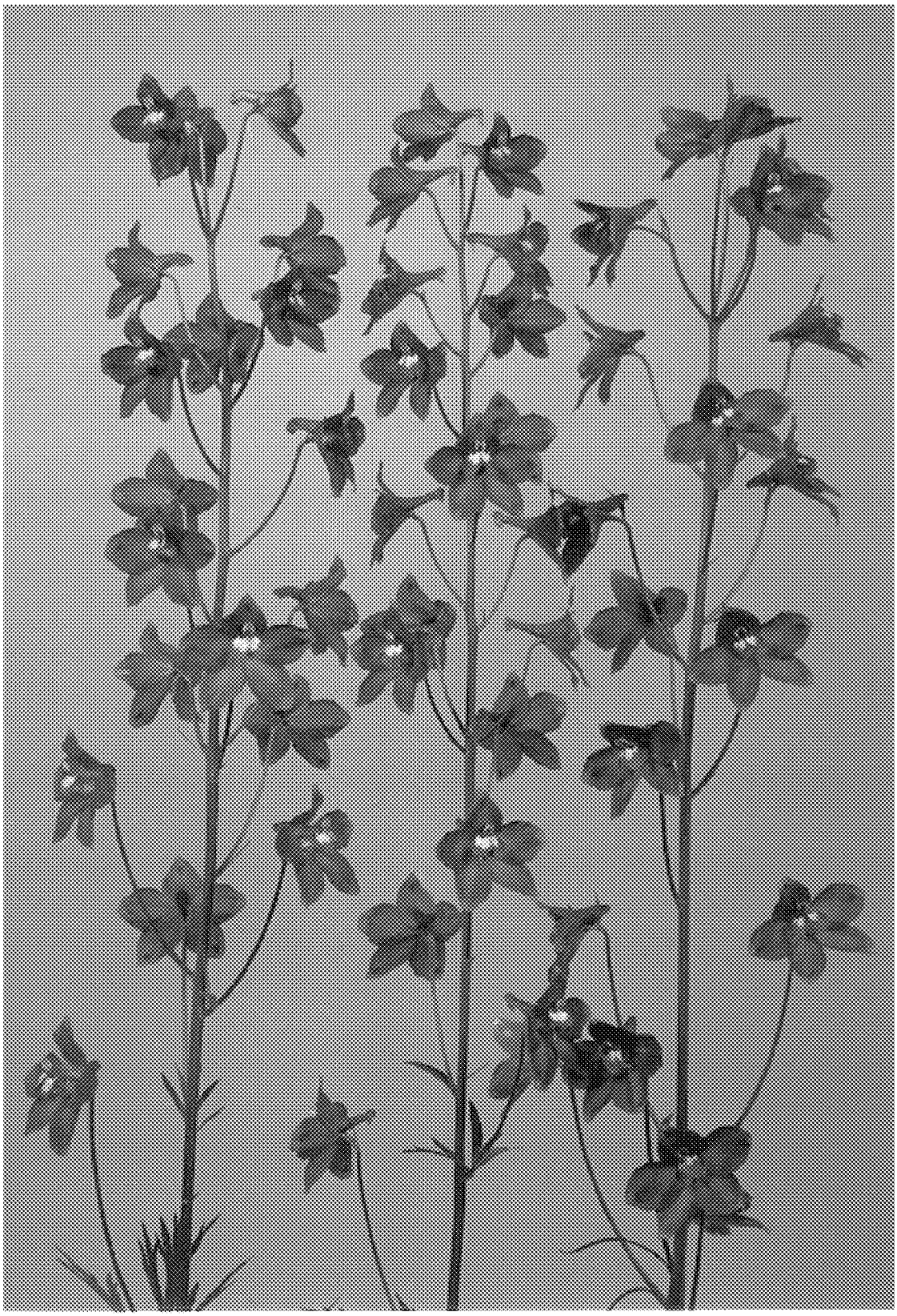
FIG. 1 is a photograph showing an inflorescence (flowering stalk) of the delphinium of the invention as a whole.
Figure 2:
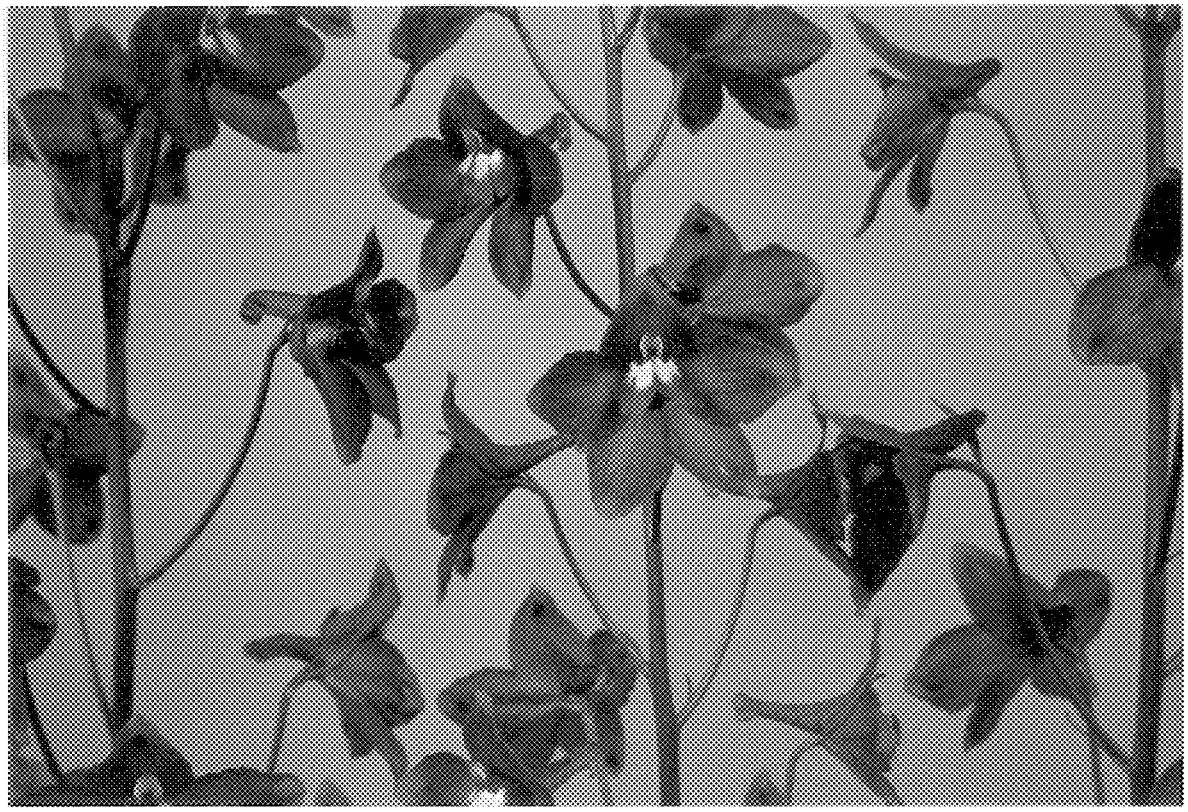
FIG. 2 is a photograph showing the flower portion of the delphinium of the invention.

The plant type falls under "upright" when classified into "upright", "medium" or "wide spreading". The plant height is about 150.5 cm, which is rather tall among delphiniums.

Stem

The stem is about 81.5 cm in length, which is rather long among delphiniums. The stem is about 0.9 cm in diameter. The stem has hair assuming a grayish green color (Japanese Horticultural Standard, JHS Color Chart No. 3513, Royal Horticultural Society, R.H.S., Colour Chart No. 144-B moderate yellow green).

Leaf

The average number of leaves per individual stem at the time of flowering is about 24.0. The leaf length is about 19.5 cm; the leaf width is about 22.0 cm; and the leaf thickness is about 0.4 mm. The leaf width is rather wide among delphiniums. Each leaf has a petiole about 11.5 cm in length, which is rather long among delphiniums. There is hair at the leaf edge. The leaf surface has a dark green color (JHS Color Chart No. 3708, R.H.S. Colour Chart No. 139-A dk. olive green), and the leaf undersurface has a grayish green color (JHS Color Chart No. 3715, R.H.S. Colour Chart No. 137-B). The leaves have a compound, irregularly, deeply serrated palmate shape. The margin of the leaves is entire with a fine cilium that can be felt with the hand and the venation is pinnate and green in color.

Flower

The inflorescence is about 68.0 cm in length, which is rather long among delphiniums, and is about 15.5 cm in width. The average number of florets borne on each inflorescence is about 25.5. This density is rather low among delphiniums.

The flowering type falls under "normal type" when classified into "normal type" (wherein the florets are open) or "holding type" (wherein the florets are more closed). The flower form falls under "single flowered" when classified into "single flowered", "semi-double flowered" or "double flowered". The total diameter size of the calyx is about 5.0 cm. The length of pedicel is about 9.0 cm, which is rather long among delphiniums. The color of the pedicel is moderate yellow green, JHS Color Chart No. 3513, R.H.S. Colour Chart No. 144-A.

The number of sepals is about 5.0, which number is rather small among delphiniums. Sepals have no hair. The whole shape of the outermost sepals falls under "oval" when classified into "linear", "elliptical", "oblong", "rhombate", "oval" or "orbicular". The outermost sepal is about 2.6 cm in length and about 1.8 cm in width. The surface of the outermost sepal has a vivid purple color, more specifically, the color classified as No. 8306 in JHS Color Chart, which corresponds to R.H.S. Colour Chart No. 89-B. The coloring of green at the tip of the undersurface of the outermost sepal is definite. The sepal spur is about 1.5 cm in length, which is rather short among delphiniums, and about 0.7 cm in diameter, which is rather thick among delphiniums.

The sepal spur has a brilliant purple color, more specifically, the color classified as No. 8305 in JHS Color Chart, which corresponds to R.H.S. Colour Chart No. 90-C.

The average number of petals is about 2.0, which is rather small among delphiniums. Each petal has a spur. The color of the petals is mainly vivid purple (JHS Color Chart No. 8306, R.H.S. Colour Chart No. 89-B) and brilliant yellow (JHS Color Chart No. 2204, R.H.S. Colour Chart No. 13-A) and light yellow (JHS Color Chart No. 2503, R.H.S. Colour Chart No. 4-D) are included as secondary colors. The hair on the petal surface has a yellow color. The anther has a greenish brown color. The flowers have no fragrance.

Reproductive Organs

The florets of the present delphinium have 32 stamens and an elliptically shaped anther. The stigma is Y-shaped and light yellow in color (JHS Colour Chart No. 2504, R.H.S. Colour Chart No. 4-C). The style is brilliant yellow in color JHS Color Chart No. 2204, R.H.S. Colour Chart No. 15-B).

Other

The delphinium of the invention is a perennial and is propagated by tissue culture. The time of flowering is rather early among delphiniums. Flowers are resistant to dropping. Both the cold tolerance and heat tolerance of this delphinium are medium. Both the disease resistance and insect resistance of this delphinium are strong. The present delphinium begins flowering in May or June and continues to flower through September, in Japan.

We claim:

1. A new and distinct delphinium plant as substantially illustrated and described herein.

* * * * *